(12) United States Patent
Brannan

(10) Patent No.: US 8,328,799 B2
(45) Date of Patent: Dec. 11, 2012

(54) ELECTROSURGICAL DEVICES HAVING DIELECTRIC LOADED COAXIAL APERTURE WITH DISTALLY POSITIONED RESONANT STRUCTURE

(75) Inventor: Joseph D. Brannan, Erie, CO (US)

(73) Assignee: Vivant Medical, Inc., Boulder, CO (US)

( * ) Notice: Subject to any disclaimer, the term of this patent is extended or adjusted under 35 U.S.C. 154(b) by 604 days.

(21) Appl. No.: 12/535,851

(22) Filed: Aug. 5, 2009

(65) Prior Publication Data

US 2011/0034917 A1    Feb. 10, 2011

(51) Int. Cl.
*A61B 18/18* (2006.01)

(52) U.S. Cl. ............... 606/41; 607/154; 607/156

(58) Field of Classification Search ............ 606/32, 606/33, 41, 34; 607/101, 154, 156, 100
See application file for complete search history.

(56) References Cited

U.S. PATENT DOCUMENTS

| | | | |
|---|---|---|---|
| 4,674,481 A | 6/1987 | Boddie, Jr. et al. | |
| 4,776,086 A * | 10/1988 | Kasevich et al. | 29/828 |
| 4,823,812 A * | 4/1989 | Eshel et al. | 607/156 |
| 4,825,880 A | 5/1989 | Stauffer et al. | |
| 5,300,068 A | 4/1994 | Rosar et al. | |
| 5,957,969 A * | 9/1999 | Warner et al. | 607/156 |
| 6,016,452 A | 1/2000 | Kasevich | |
| 6,245,062 B1 * | 6/2001 | Berube et al. | 606/33 |
| 6,398,781 B1 | 6/2002 | Goble et al. | |
| 6,582,427 B1 | 6/2003 | Goble et al. | |
| 6,878,147 B2 | 4/2005 | Prakash et al. | |
| 7,194,297 B2 | 3/2007 | Talpade et al. | |
| 7,301,131 B2 * | 11/2007 | Gauthier et al. | 219/679 |
| 7,311,703 B2 * | 12/2007 | Turovskiy et al. | 606/33 |
| 2002/0022836 A1 * | 2/2002 | Goble et al. | 606/34 |
| 2003/0083654 A1 * | 5/2003 | Chin et al. | 606/41 |
| 2003/0153908 A1 | 8/2003 | Goble et al. | |
| 2006/0155270 A1 * | 7/2006 | Hancock et al. | 606/33 |
| 2006/0293651 A1 | 12/2006 | Cronin | |
| 2010/0049185 A1 * | 2/2010 | Paulus | 606/33 |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |

(Continued)

OTHER PUBLICATIONS

International Search Report EP10008139 dated Nov. 30, 2010.

(Continued)

*Primary Examiner* — Michael Peffley
*Assistant Examiner* — Jocelyn D Ram

(57) ABSTRACT

An electrosurgical device for directing energy to a target volume of tissue includes a coaxial feedline having an inner conductor, an outer conductor and a dielectric material disposed therebetween. A proximal cylindrical dielectric sleeve is coupled to the inner conductor at a distal end of the coaxial feedline. A distal cylindrical dielectric sleeve is coupled to the inner conductor. First and second dielectric segments are coupled to the inner conductor and disposed between the proximal cylindrical dielectric sleeve and the distal cylindrical dielectric sleeve. The device also includes an elongated shaft overlying the proximal cylindrical dielectric sleeve, the first dielectric segment, the second dielectric segment and the distal cylindrical dielectric sleeve. The elongated shaft includes an opening defined therethrough, wherein the opening is at least partially aligned with the first dielectric segment. A balun structure is disposed on the elongated shaft, at least partially overlying the opening in the elongated shaft.

15 Claims, 7 Drawing Sheets

FOREIGN PATENT DOCUMENTS

| | | |
|---|---|---|
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 034 748 | 9/2000 |
| EP | 1 055 400 | 11/2000 |
| EP | 1 159 926 | 5/2001 |
| EP | 2158869 | 3/2010 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | 00/53112 | 9/2000 |
| WO | 03/039385 | 5/2003 |

OTHER PUBLICATIONS

U.S. Appl. No. 09/195,118, filed Nov. 18, 1998, Patent 6451015.
U.S. Appl. No. 10/244,346, filed Sep. 16, 2002, Abandoned.
U.S. Appl. No. 11/053,987, filed Feb. 8, 2005, Patent 7875024.
U.S. Appl. No. 12/023,606, filed Jan. 31, 2008.
U.S. Appl. No. 12/129,482, filed May 29, 2008, Patent 8059059.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009, Patent 7642451.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009, Patent 8118808.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009, Patent 8035570.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.

C. H. Dumey et al., "Antennas for Medical Applications", Antenna Handbook: Theory Application and Design, p. 24-40, Van Nostrand Reinhold, 1988 New York, V.T. Lo, S.W. Lee.

Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.

Carus et al., "Initial Experience With the LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthennia in Cancer Therapy," Chapter 94In Biologic Effects of Nonionizing Electromagnetic Fields, CRC Press, Inc., pp. 1424-1428.

Chung et al., "Clinical Experience of Sutureless Closed Hemorrhoidectomy with LigaSure™" Diseases of the Colon & Rectum, vol. 46, No. 1, Jan. 2003.

Cosman et al., "Radiofrequency Lesion Generation and its Effect on Tissue Impedence", Applied Neurophysiology, 51:230-242, 1988.

Cosman et al., "Theoretical Aspects of Radiofrequency Lesions in the Dorsal Root Entry Zone" Neurosurgery 15:(1984), pp. 945-950.

Cosman et al., "Methods of Making Nervous System Lesions" In William RH, Rengachary SS (eds): Neurosurgery, New York: McGraw- Hill, vol. 111, (1984), pp. 2490-2499.

Surgery Crawford et al., "Use of the LigaSure™ Vessel Sealing System in Urologic Cancer Surgery" Grand Rounds in Urology 1999, vol. 1, Issue 4, pp. 10-17.

E. David Crawford, "Use of a Novel Vessel Sealing Technology in Management of the Dorsal Veinous Complex" Sales/Product Literature 2000.

Esterline Product Literature, "Light Key: Visualize a Virtual Keyboard. One With No Moving Parts", 4 pages.

Esterline, "Light Key Projection Keyboard" 2004 Advanced Input Systems, located at: <http://www.advanced-input.com/lightkey> last visited on Feb. 10, 2005.

Geddes et al., "The Measurement of Physiologic Events by Electrical Impedence" Am. J. Ml, Jan. Mar. 1964, pp. 16-27.

Goldberg et al., "Image-guided Radiofrequency Tumor Ablation: Challenges and Opportunities—Part I", (2001) J Vasc. lnterv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Heniford et al., "Initial Results with an Electrothermal Bipolar Vessel Sealer" Surgical Endoscopy (2001) 15:799-801.

Herman et al., "Laparoscopic Intestinal Resection With the LigaSure™ Vessel Sealing System: A Case Report" Innovations That Work, Feb. 2002.

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Johnson et al., "Evaluation of a Bipolar Electrothermal Vessel Sealing Device in Hemorrhoidectomy" Sales/Product Literature, Jan. 2004.

Jarrett et al., "Use of the LigaSure™ Vessel Sealing System for Peri-Hilar Vessels in Laparoscopic Nephrectomy" Sales/Product Literature 2000.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, " LigaSure™ System Used in Laparoscopic 1st and 2nd Stage Orchiopexy" Innovations That Work, Nov. 2002.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210, Abstract only.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Mar. 2000) I'D Wire: product description, 1 page.

MDTECH product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. 1-1, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184, abstract only.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. 1, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thennotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (1 PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar vessel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
S. Humphries Jr. et al., "Finite Element Codes to Model Electrical Heating and Nonlinear Thermal Transport in Biological Media", Proc. ASME HTD-355, 131 (1997).
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electrosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.

European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/USO4/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
European Search Report EP 05013895 dated Oct. 21, 2005.
Paul G. Horgan, "A Novel Technique for Parenchymal Division During Hepatectomy" The American Journal of Surgery, vol. 181, No. 3, Apr. 2001, pp. 236-237.
Johnson, "Evaluation of the LigaSure™ Vessel Sealing System in Hemorrhoidectormy" American College of Surgeons (ACS) Clinic La Congress Poster (2000).
E. David Crawford, "Evaluation of a New Vessel Sealing Device in Urologic Cancer Surgery" Sales/Product Literature 2000.
U.S. Appl. No. 08/483,742, filed Jun. 7, 1995.
U.S. Appl. No. 08/136,098, filed Oct. 14, 1993.
Dulemba et al., "Use of a Bipolar Electrothermal Vessel Sealer in Laparoscopically Assisted Vaginal Hysterectomy" Sales/Product Literature; Jan. 2004.
Anonymous. (1999) Auto Suture MIBB Site Marker; Single Use Clip Applier, United States Surgical (Product instructions), 2 pages.

\* cited by examiner

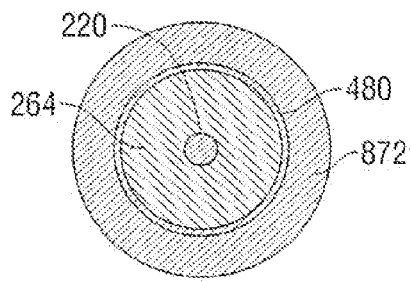
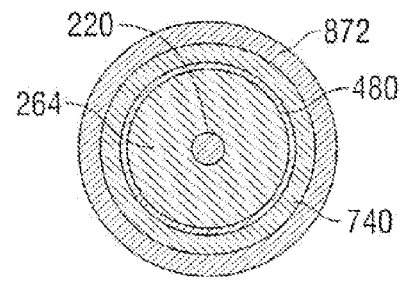
FIG. 10A    FIG. 10B
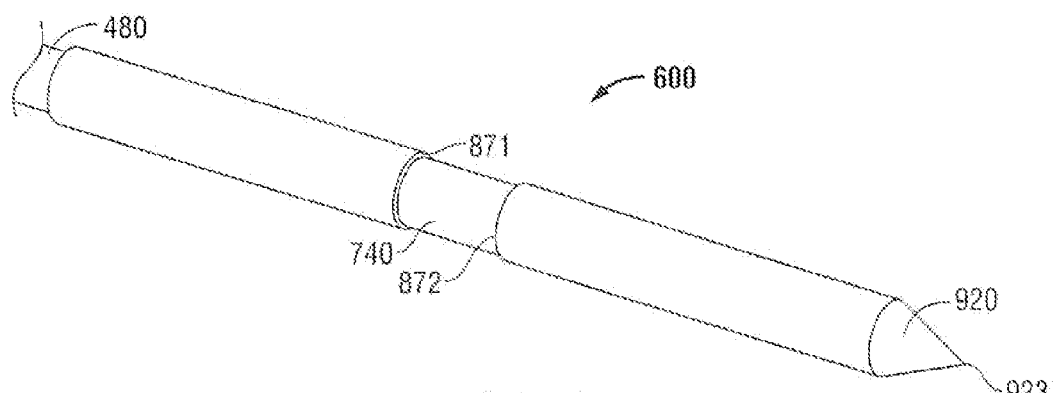
FIG. 11
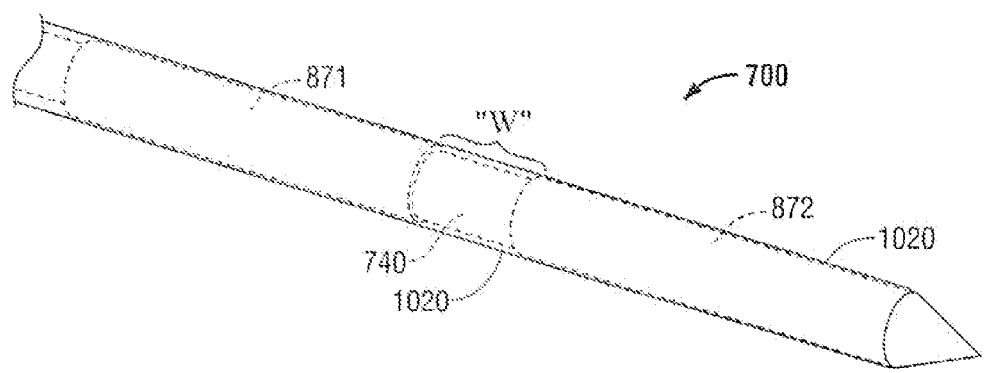
FIG. 12

ELECTROSURGICAL DEVICES HAVING DIELECTRIC LOADED COAXIAL APERTURE WITH DISTALLY POSITIONED RESONANT STRUCTURE

BACKGROUND

1. Technical Field

The present disclosure relates to electrosurgical devices suitable for use in tissue ablation applications and, more particularly, to electrosurgical devices having a dielectric loaded coaxial aperture with a distally positioned resonant structure.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis.

A microwave transmission line typically includes a thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, e.g., a length of transmission line or coaxial cable, is provided with a plurality of openings through which energy "leaks" or radiates away from the guiding structure. This type of construction is typically referred to as a "leaky coaxial" or "leaky wave" antenna.

Some ablation targeted lesions are too small or too hard to be punctured by an ablation probe. In these cases, doctors may place the probe as close as possible to the lesion and perform an ablation. With non-directional ablation probes, the ablation may radiate to both sides of the probe which may damage healthy tissue located on the non-tumor side of the radiating section.

During certain procedures, it can be difficult to assess the extent to which the microwave energy will radiate into the surrounding tissue, making it difficult to determine the area or volume of surrounding tissue that will be ablated.

SUMMARY

The present disclosure relates to a device for directing energy to a target volume of tissue including a coaxial feedline having an inner conductor, an outer conductor coaxially disposed around the inner conductor, and a dielectric material disposed therebetween. The device includes a first dielectric segment coupled to the inner conductor and a second dielectric segment coupled to the inner conductor. The device also includes an elongated shaft overlying at least a portion of the second dielectric segment, the elongated shaft having an opening defined therethrough, the opening at least partially aligned with the first dielectric segment. A balun structure is disposed on the elongated shaft, the balun structure at least partially overlying the opening in the elongated shaft.

The present disclosure relates to a device for directing energy to a target volume of tissue including a coaxial feedline having an inner conductor, an outer conductor coaxially disposed around the inner conductor, and a dielectric material disposed therebetween. The device includes a proximal cylindrical dielectric sleeve coupled to the inner conductor at a distal end of the coaxial feedline, and a distal cylindrical dielectric sleeve coupled to the inner conductor. First and second dielectric segments are coupled to the inner conductor, wherein the first and second dielectric segments are disposed between the proximal cylindrical dielectric sleeve and the distal cylindrical dielectric sleeve. The device also includes an elongated shaft overlying the proximal cylindrical dielectric sleeve, the first dielectric segment, the second dielectric segment and the distal cylindrical dielectric sleeve. The elongated shaft includes an opening defined therethrough, wherein the opening is at least partially aligned with the first dielectric segment. A balun structure is disposed on the elongated shaft, at least partially overlying the opening in the elongated shaft.

The present disclosure also relates to a method for manufacturing an electrosurgical device including the step of providing a coaxial feedline having an inner conductor, an outer conductor, and a dielectric material disposed therebetween, and joining a first dielectric member to a portion of the inner conductor extending beyond the dielectric material and the outer conductor at a distal end of the coaxial feedline. The method also includes the steps of: joining a second dielectric member to a portion of the inner conductor extending beyond the first dielectric member at a distal end of the first dielectric member; joining a third dielectric member to the portion of the inner conductor extending beyond the first dielectric member at a distal end of the first dielectric member; joining a fourth dielectric member to a portion of the inner conductor extending beyond the second and third dielectric members at a distal end of the second and third dielectric members; positioning an elongated shaft overlying the first, second, third and fourth dielectric members, the elongated shaft having an opening defined therethrough, the opening aligned with the third dielectric member; and forming a balun onto the elongated shaft, the balun including a first balun outer conductor and a second balun outer conductor, each of the first and second balun outer conductors disposed partially overlying the opening in the elongated shaft.

BRIEF DESCRIPTION OF THE DRAWINGS

Objects and features of the presently disclosed antenna assemblies will become apparent to those of ordinary skill in the art when descriptions of various embodiments thereof are read with reference to the accompanying drawings, of which:

FIG. 10A is a cross-sectional view of a distal portion of the energy applicator of FIG. 9 according to an embodiment of the present disclosure;

FIG. 10B is a cross-sectional view of another distal portion of the energy applicator of FIG. 9 according to an embodiment of the present disclosure;

FIG. 11 is a partial, perspective view of the energy applicator of FIG. 9 shown with a tapered portion extending distally of the distal electrically-conductive sleeve member according to an embodiment of the present disclosure;

FIG. 12 is a partial, perspective view of the energy applicator of FIG. 11 shown with a layer disposed along the length of the elongated shaft and overlying the proximal and distal electrically-conductive sleeve members and bridging the gap therebetween according to an embodiment of the present disclosure;

DETAILED DESCRIPTION

Figure 1:
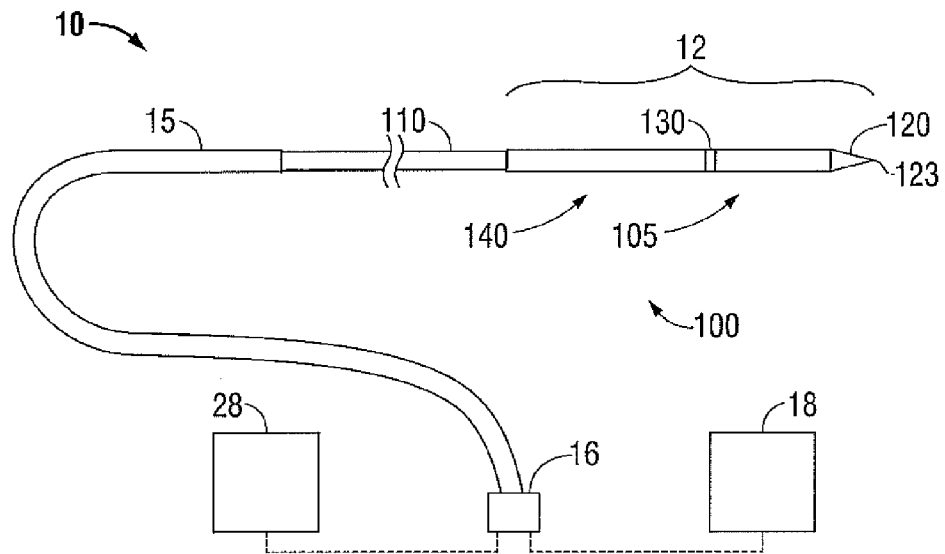
FIG. 1 is a schematic diagram of an ablation system according to an embodiment of the present disclosure.

Hereinafter, embodiments of the presently disclosed electrosurgical device with a directional radiation pattern will be described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus that is closer to the user and the term "distal" refers to that portion of the apparatus that is further from the user.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation assisted resection. As it is used in this description, "transmission line" generally refers to any transmission medium that can be used for the propagation of signals from one point to another.

Various embodiments of the present disclosure provide electrosurgical devices for treating tissue and methods of directing electromagnetic radiation to a target volume of tissue. Embodiments may be implemented using electromagnetic radiation at microwave frequencies or at other frequencies. An electrosurgical system including an energy applicator, according to various embodiments, is designed and configured to operate between about 500 MHz and about 10 GHz with a directional radiation pattern.

Various embodiments of the presently disclosed electrosurgical device with a directional radiation pattern are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna.

FIG. 1 shows an electrosurgical system 10, according to an embodiment of the present disclosure, which includes an energy applicator or probe 100. Probe 100 generally includes an antenna assembly 12 having a radiating portion connected by a feedline 110 (or shaft) via a transmission line 15 to a connector 16, which may further operably connect the probe 100 to a power generating source 28, e.g., a microwave or RF electrosurgical generator.

Feedline 110 may electrically connect the antenna assembly 12 via the transmission line 15 to the generator 28 and may include a coaxial cable, which may be semi-rigid or flexible. Feedline 110 may have a variable length from a proximal end of the antenna assembly 12 to a distal end of transmission line 15 ranging from a length of about one inch to about ten inches. Feedline 110 may be constructed of a variety of electrically conductive materials, e.g., copper, gold, or other conductive metals with similar conductivity values. Feedline 110 may be made of stainless steel, which generally offers the strength required to puncture tissue and/or skin. Conductive materials used to form the feedline 110 may be plated with other materials, e.g., other conductive materials, to improve their properties, e.g., to improve conductivity or decrease energy loss, etc. In some embodiments, the feedline 110 includes stainless steel, and to improve its conductivity, the stainless steel may be coated with a layer of a conductive material such as copper or gold. Feedline 110 may include an inner conductor, a dielectric material coaxially surrounding the inner conductor, and an outer conductor coaxially surrounding the dielectric material. Antenna assembly 12 may be formed from a portion of the inner conductor that extends distal of the feedline 110 into the antenna assembly 12. Feedline 110 may be cooled by fluid e.g., saline or water, to improve power handling, and may include a stainless steel catheter.

In some embodiments, the power generating source 28 is configured to provide microwave energy at an operational frequency from about 500 MHz to about 2500 MHz. In other embodiments, the power generating source 28 is configured to provide microwave energy at an operational frequency from about 500 MHz to about 10 GHz. Power generating source 28 may be configured to provide various frequencies of electromagnetic energy. Transmission line 15 may additionally, or alternatively, provide a conduit (not shown) configured to provide coolant from a coolant source 18 to the probe 100.

Located at the distal end of the antenna assembly 12 is an end cap or tapered portion 120, which may terminate in a sharp tip 123 to allow for insertion into tissue with minimal resistance. One example of a straight probe with a sharp tip that may be suitable for use as the energy applicator 100 is commercially available under the trademark EVIDENT™ offered by Covidien. The end cap or tapered portion 120 may include other shapes, such as, for example, a tip 123 that is rounded, flat, square, hexagonal, or cylindroconical.

In some variations, the antenna assembly 12 includes a distal radiating portion 105 and a proximal radiating portion 140. In some embodiments, a junction 130 couples the proximal radiating portion 140 and the distal radiating portion 105.

In some embodiments, the distal and proximal radiating portions 105, 140 align at the junction 130, which is generally made of a dielectric material, e.g., adhesives, and are also supported by the inner conductor that extends at least partially through the distal radiating portion 105. Junction 130, or portions thereof, may be disposed between the proximal and distal radiating portions, 140 and 105. Junction 130 may be formed from any suitable elastomeric or ceramic dielectric material by any suitable process. In some embodiments, the junction 130 is formed by overmolding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E. I. du Pont de Nemours and Company of Wilmington, Del., United States). Junction 130 may be formed using any suitable overmolding compound by any suitable process, and may include use of a ceramic substrate.

In some embodiments, the antenna assembly 12 may be provided with a coolant chamber (not shown). Additionally, the junction 130 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703 entitled "DEVICES AND METHODS FOR COOLING MICROWAVE ANTENNAS".

In some embodiments, the antenna assembly 12 may be provided with an outer jacket (not shown) disposed about the distal radiating portion 105, the junction 130 and/or the proximal radiating portion 140. The outer jacket may be formed of any suitable material, such as, for example, polymeric or ceramic materials. The outer jacket may be applied by any suitable method, such as, for example, heat shrinking, overmolding, coating, spraying dipping, powder coating, baking and/or film deposition. The outer jacket may be a water cooled catheter formed of a material having low electrical conductivity.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or atop tissue, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may provide ablations in short procedure times, e.g., a few minutes, to destroy cancerous cells in the target tissue region.

A plurality of probes 100 may be placed in variously arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, time and wattage.

In operation, microwave energy having a wavelength, lamda (λ), is transmitted through the antenna assembly 12, e.g., along the proximal and distal radiating portions 140, 105, and radiated into the surrounding medium, e.g., tissue. The length of the antenna for efficient radiation may be dependent on the effective wavelength, $\lambda_{eff}$, which is dependent upon the dielectric properties of the medium being radiated into. Antenna assembly 12 through which microwave energy is transmitted at a wavelength, λ, may have differing effective wavelengths, $\lambda_{eff}$, depending upon the surrounding medium, e.g., liver tissue, as opposed to, e.g., breast tissue.

FIGS. 2 through 12 show a sequentially-illustrated, assembly of components forming an energy applicator or probe having a dielectric loaded coaxial aperture (e.g., "W" shown in FIG. 12) with distally positioned resonant structure (e.g., 909 shown in FIG. 9), in accordance with the present disclosure.

According to an embodiment of the present disclosure, an energy applicator or probe (shown generally as 200 in FIGS. 2 and 3) is provided with a coaxial feedline 226 having an inner conductor 220 that extends along the longitudinal axis "A" of the energy applicator 200, an outer conductor 224 coaxially disposed about the inner conductor 220, and a dielectric material 222 disposed therebetween. In some embodiments, the inner conductor 220 has a diameter "$D_1$" and the dielectric material 222 has an outer diameter "$D_2$".

At the distal end of the feedline 226, a portion of the dielectric material 222 may extend beyond the outer conductor 224. Additionally, or alternatively, a portion of the inner conductor 220 (e.g., 22 shown in FIG. 2) may extend beyond the dielectric material 222 and the outer conductor 224. In some embodiments, the antenna assembly 12, or portions thereof, may be coupled to the inner conductor portion 22. Alternatively, the antenna assembly 12, or portions thereof, may be coupled to an elongated conductor (e.g., similar to the inner conductor portion 22), wherein the elongated conductor is electrically coupled to the inner conductor 220 of the feedline 226.

Figure 2:
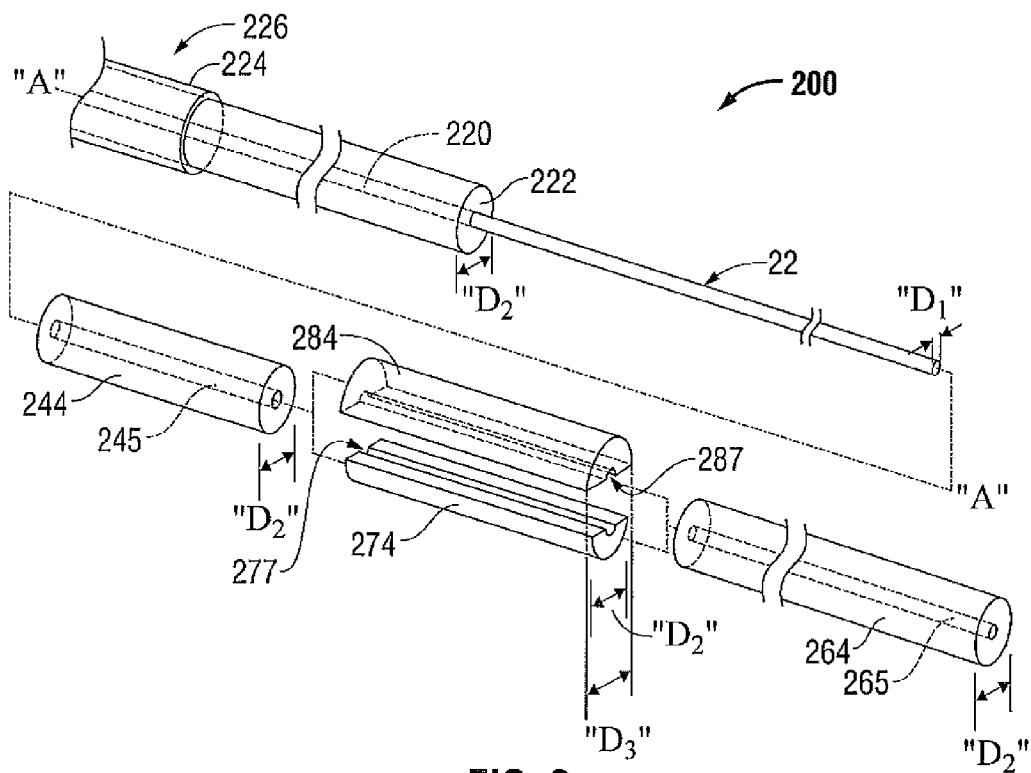
FIG. 2 is a perspective view with parts disassembled of a portion of an energy applicator according to an embodiment of the present disclosure.
Figure 3:
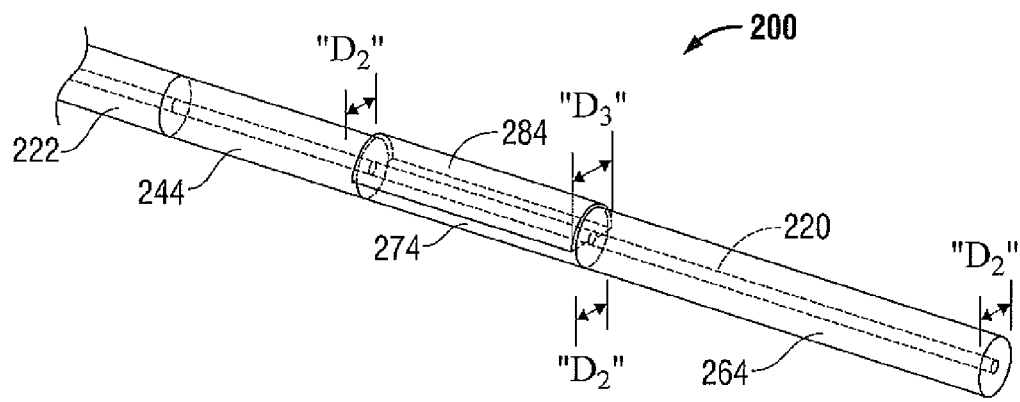
FIG. 3 is a perspective assembled view of the portion of the energy applicator shown in FIG. 2 according to an embodiment of the present disclosure.

As shown in FIGS. 2 and 3, a proximal cylindrical dielectric sleeve 244 may be coupled to the inner conductor 220 at a distal end of the coaxial feedline 226. Additionally, or alternatively, a first dielectric segment 284 and a second dielectric segment 274 may be coupled to the inner conductor 220. Additionally, or alternatively, a distal cylindrical dielectric sleeve 264 may be coupled to the inner conductor 220.

Proximal cylindrical dielectric sleeve 244, first dielectric segment 284 and a second dielectric segment 274 may be formed from dielectric materials that provide an impedance match from the coaxial feedline 226. First dielectric segment 284 may be formed from a material with a dielectric constant that is higher than the dielectric constant of the second dielectric segment 274, e.g., to maximize energy radiated into the surrounding medium, e.g., tissue.

In some embodiments, a proximal cylindrical dielectric sleeve 244, having a diameter "$D_2$", is coupled to the inner conductor 220. Proximal cylindrical dielectric sleeve 244 may be configured with a central channel 245 extending longitudinally therethrough to accommodate the inner conductor 220. Proximal cylindrical dielectric sleeve 244 may be formed from any suitable dielectric material. In some embodiments, the proximal cylindrical dielectric sleeve 244 is formed from a material with a dielectric constant in the range of about 2 to about 10.

In some embodiments, a distal cylindrical dielectric sleeve 264, having a diameter "$D_2$", is coupled to the inner conductor 220. Distal cylindrical dielectric sleeve 264 may be formed from any suitable dielectric material. Distal cylindrical dielectric sleeve 264 may be disposed distally of the proximal cylindrical dielectric sleeve 244 and may be configured with a central channel 265 extending longitudinally therethrough to accommodate the inner conductor 220. In some embodiments, the distal cylindrical dielectric sleeve 264 is formed from a material with a dielectric constant different than the dielectric constant of the proximal cylindrical dielectric sleeve 244. Distal cylindrical dielectric sleeve 264 may be a high dielectric material, e.g., a material with a dielectric constant in the range of about 3 to about 50, to shorten the effective wavelength, $\lambda_{eff}$, of energy.

Figure 4:
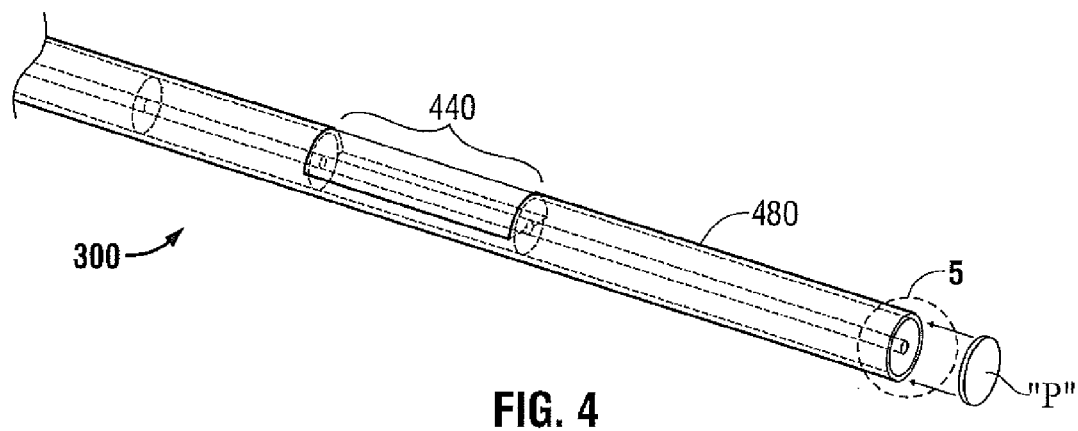
FIG. 4 is a perspective, partly separated view of the portion of the energy applicator of FIG. 3 provided with an elongated shaft having an opening therethrough and an end cap according to an embodiment of the present disclosure.
Figure 5:
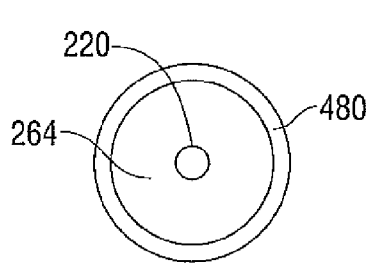
FIG. 5 is an enlarged view of the indicated area of detail of FIG. 4 according to an embodiment of the present disclosure.
Figure 6:
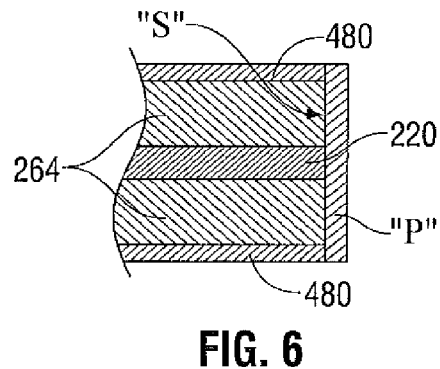
FIG. 6 is a partial, cross-sectional view of the energy applicator of FIG. 7 according to an embodiment of the present disclosure.

The length of the distal cylindrical dielectric sleeve 264 may be varied, depending on the dielectric constant of the material selected, to allow positioning of a radiating aperture (e.g., "W" shown in FIGS. 12 and 13) at a quarter wavelength (or half wavelength, etc.) from a distal short (e.g., "P" shown in FIGS. 4 and 6). For example, the physical length of the distal cylindrical dielectric sleeve 264 for a selected dielectric constant to allow positioning of an aperture at a selected wavelength from a distal short may be calculated using Equation 1.

$$\lambda = \frac{c}{f\sqrt{\varepsilon_r}}, \qquad (1)$$

where c is the speed of light, f is the frequency, and $\varepsilon_r$ is the dielectric constant. For example, in a case where an aperture is to be positioned at a quarter wavelength, given a dielectric sleeve having a dielectric constant $\varepsilon_r$, using Equation 1, the length l of the dielectric sleeve is calculated as:

$$l = \frac{\lambda}{4} = \frac{c}{4f\sqrt{\varepsilon_r}}.$$

In some embodiments, a first dielectric segment 284 and a second dielectric segment 274 are coupled to the inner conductor 220. As shown in FIG. 25 the first and second dielectric segments 284, 274 may be disposed between the proximal cylindrical dielectric sleeve 244 and the distal cylindrical dielectric sleeve 264. First and second dielectric segments 284, 274 generally include one or more flat planar surfaces and a partial cylindrical surface. The shape and size of the first and second dielectric segments 284, 274 may be varied from the configuration depicted in FIGS. 2 through 4 (see, e.g., 1564, 1562 and 1664, 1662 shown in FIGS. 15 and 16, respectively). In some embodiments, the first dielectric segment 284 is formed from a material with a dielectric constant in the range of about 2 to about 30. In some embodiments, the second dielectric segment 274 is formed from a material with a dielectric constant in the range of about 2 to about 30.

In some embodiments, the first dielectric segment 284 has a substantially half-cylindrical shape, having a diameter "$D_3$", and includes a flat planar surface configured with a recess in the form of a groove 287 extending longitudinally across the flat planar surface. In some embodiments, the second dielectric segment 274 has a substantially half-cylindrical shape, having a diameter "$D_2$", and includes a flat planar surface configured with a recess in the form of a groove 277 extending longitudinally across the flat planar surface.

Grooves 287 and 277 may be configured to accommodate a portion of the inner conductor 220. In some embodiments, when the first and second dielectric segments 284, 274 are coupled to the inner conductor 220, the respective flat planar surfaces of the first and second dielectric segments 284, 274 contact one another. The shape and size of the grooves 287 and 277 may be varied from the configuration depicted in FIG. 2.

FIGS. 4 through 7 show an energy applicator 300, according to an embodiment of the present disclosure, which is similar to the energy applicator 200 of FIG. 3, except for an elongated shaft 480 (outlined in bold lines in FIG. 4) having an opening 440 therethrough, and an end cap "P" disposed distally to the distal end of the elongated shaft 480. In some embodiments, the elongated shaft 480 has an inner diameter "$D_2$" and an outer diameter "$D_3$". As shown in FIG. 4, the end cap "P" may have a disc-or plate-like shape. End cap "P" may be formed of any suitable electrically-conductive material, e.g., metal such as stainless steel, titanium, etc. As shown in FIG. 6, the proximal surface "S" of the end cap "P" makes contact with both the distal end of the inner conductor 220 and the distal end of the elongated shaft 480, thereby forming a distal short. The shape and size of the end cap "P" may be varied from the configuration depicted in FIGS. 4 and 6.

Figure 7:
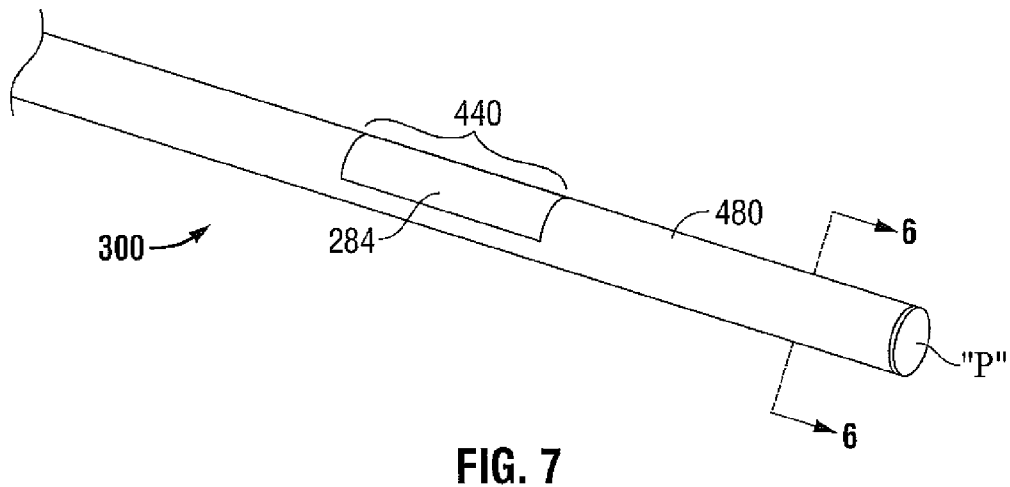
FIG. 7 is a perspective, assembled view of the portion of the energy applicator of FIG. 4 according to an embodiment of the present disclosure.

As shown in FIG. 7, the opening 440 in the elongated shaft 480 may be aligned with the first dielectric segment 284. In some embodiments, the first dielectric segment 284 and the elongated shaft 480 may be substantially concentric to a longitudinal axis (e.g., "A" shown in FIG. 2) of the energy applicator. Elongated shaft 480 may be electrically coupled to the outer conductor 224 of the coaxial feedline 226.

Opening 440 is made by removing a radial portion the elongated shaft 480 an optimized length back from the distal short. In some embodiments, the opening 440 is positioned to maximize directivity and coupling of microwave energy into tissue, e.g., opening 440 may be placed at the voltage maximum of the standing wave created by the shorted coaxial distal end. Opening 440 may be of any length and radial angle to achieve the desired amount of coax to free space coupling and radiation directivity.

The dielectric constant of dielectric materials on either side of the opening 440, proximal or distal, may vary with distance from the opening 440 to achieve impedance match and optimal energy delivery and directivity to tissue. The dielectric materials filling the coaxial structure at the site of the opening 440 may vary in dielectric constant with shells or more complex dielectric layering to achieve the optimum antenna directivity and energy to tissue delivery.

Figure 14:
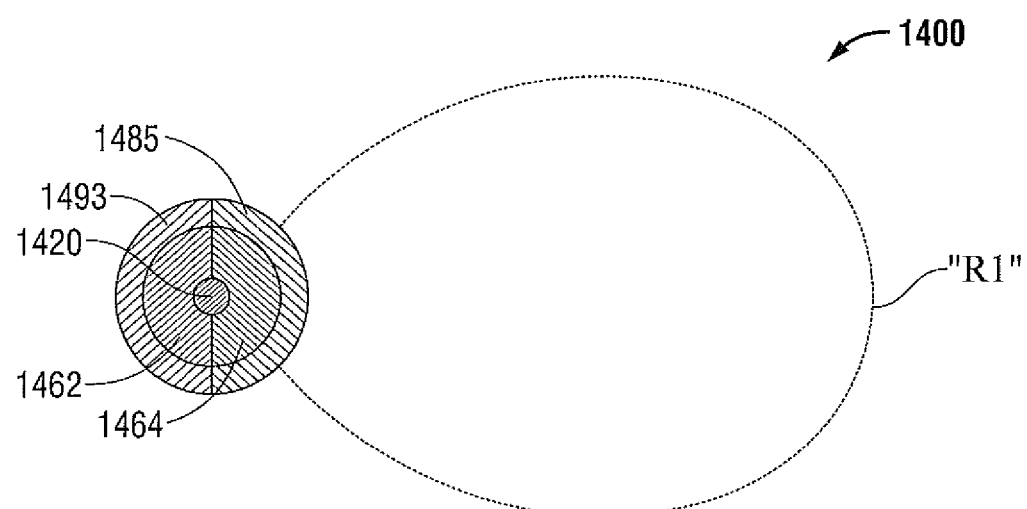
FIG. 14 is a cross-sectional view of an energy applicator shown with a diagrammatic representation of an emitted radiation pattern according to an embodiment of the present disclosure.
Figure 15:
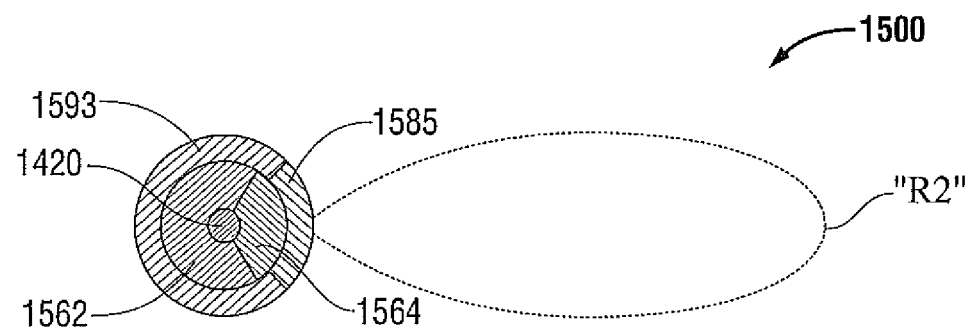
FIG. 15 is a cross-sectional view of another embodiment of an energy applicator shown with a diagrammatic representation of an emitted radiation pattern according to the present disclosure.
Figure 16:
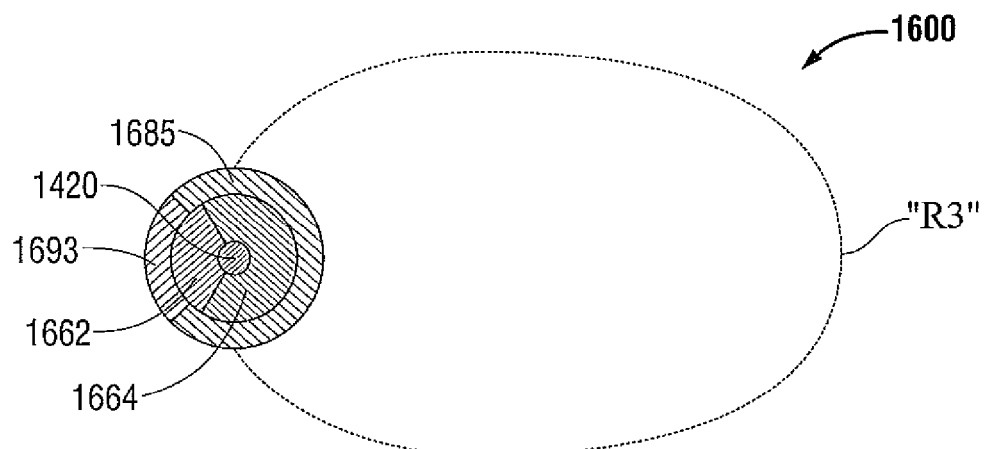
FIG. 16 is a cross-sectional view of yet another embodiment of an energy applicator shown with a diagrammatic representation of an emitted radiation pattern according to the present disclosure.

In some embodiments, the first dielectric segment 284 has a diameter "$D_2$" and the elongated shaft 480 has an outer diameter "$D_3$", where "$D_3$" is larger than "$D_2$". In such cases, the opening 440 may be filled with a nonconductive radio frequency transparent material, e.g., a glass fiber epoxy composite or polyimide. This may be accomplished in an over molding process. The window may also be created by placing a heat shrink or rigid composite sleeve along the entire antenna assembly. Some examples of dielectric material configurations at the site of the opening 440, according to some embodiments of the present disclosure, are shown in FIGS. 14 through 16.

Figure 8:
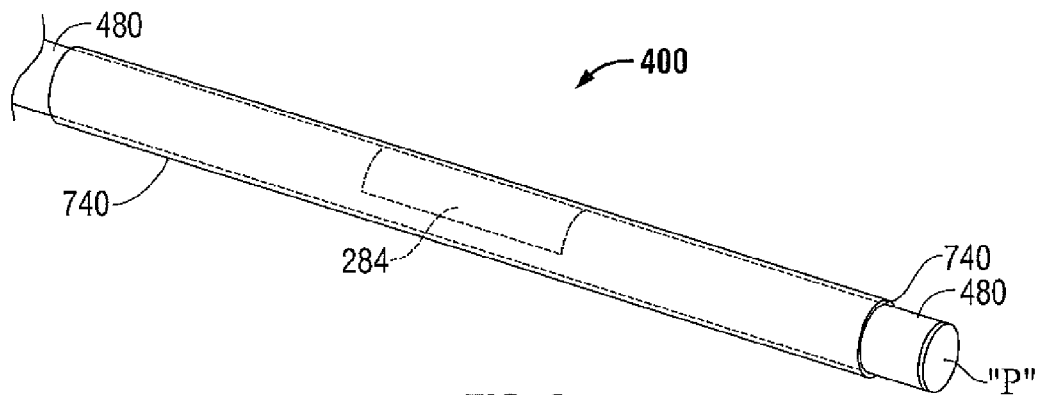
FIG. 8 is a partial, perspective view of the energy applicator of FIG. 7 shown with a dielectric sleeve member surrounding a portion of the elongated shaft including the opening in the elongated shaft, according to an embodiment of the present disclosure.

FIG. 8 shows an energy applicator 400, according to an embodiment of the present disclosure, which is similar to the energy applicator 300 of FIG. 7, except for a dielectric sleeve member 740 (also referred to herein as a balun insulator) disposed coaxially about a portion of the elongated shaft 480. Balun insulator 740 may be formed of any non-conductive insulator, e.g., a Teflon® sleeve. Balun insulator 740 may extend fully or partially over the opening 440 in the elongated shaft. In some embodiments, the balun insulator 740 extends fully over the opening 440 and the half-cylindrical dielectric member 284 disposed therein. The shape, size, and arrangement of the dielectric balun insulator 740 (e.g., its position relative to the opening 440 and/or the end cap "P") may be varied from the configuration depicted in FIG. 8. Balun insulator 740 may extend beyond the open ends of one or more electrically-conductive sleeve members (e.g., 871, 872 shown in FIG. 9) of a balun structure (e.g., 909 shown in FIG. 9) to enhance effectiveness of the balun.

Figure 9:
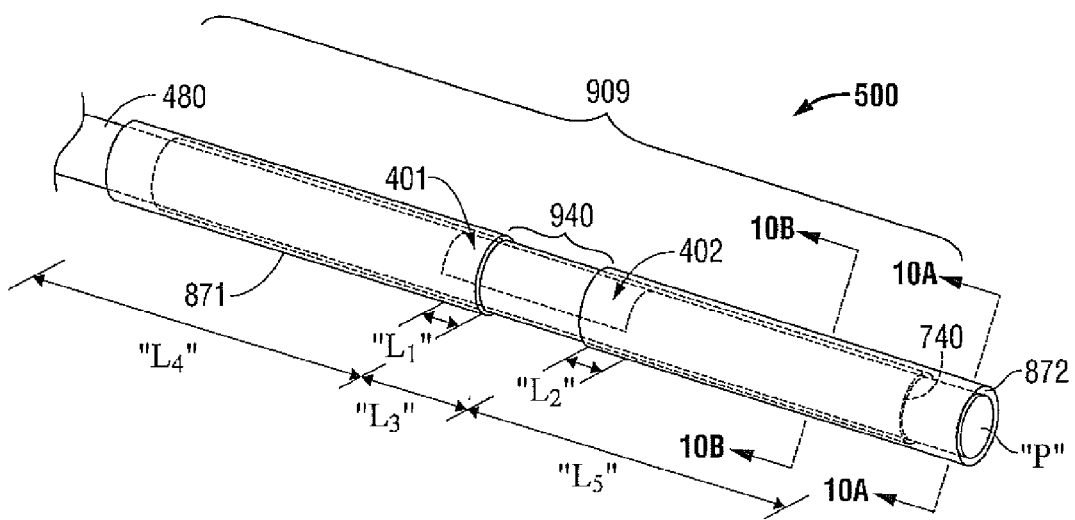
FIG. 9 is a partial, perspective view of the energy applicator of FIG. 8 shown with portions of the dielectric sleeve member and the opening in the elongated shaft (in phantom lines) surrounded by axially aligned proximal and distal electrically-conductive sleeve members having a gap therebetween according to an embodiment of the present disclosure.

FIG. 9 shows an energy applicator 500, according to an embodiment of the present disclosure, which is similar to the energy applicator 400 of FIG. 7, except for a first electrically-conductive sleeve member 871 and a second electrically-conductive sleeve member 872 (also referred to herein as balun outer conductors) axially aligned with a gap 940 therebetween. A proximal end portion of the first electrically-conductive sleeve member 871 may be coupled to a proximal portion of the elongated shaft 480. A distal end portion of the second electrically-conductive sleeve member 872 may be coupled to a distal portion of the elongated shaft 480, e.g., as shown in FIG. 10A. First and second electrically-conductive sleeve members 871, 872 may be formed of any suitable electrically-conductive material, e.g., metal such as stainless steel, aluminum, titanium, copper, etc.

First and second electrically-conductive sleeve members 871, 872 may overlap portions of the window 440 in the elongated shaft 480. As shown in FIG. 9, the first electrically-conductive sleeve member 871 may overlap a proximal portion 401, having a length "$L_1$", of the window 440, and the second electrically-conductive sleeve member 872 may overlap a distal portion 402, having a length "$L_2$", of the window 440, whereby a gap 940, having a length "$L_3$", is formed therebetween. In some embodiments, the first electrically-conductive sleeve member 871 has a length "$L_4$", wherein "$L_4$" may be a quarter wavelength or a half wavelength. In some embodiments, the second electrically-conductive sleeve member 872 has a length "$L_5$", wherein "$L_5$" may be a quarter wavelength or a half wavelength. First and second electrically-conductive sleeve members 871, 872 may have any suitable length.

FIG. 11 shows an energy applicator 600, according to an embodiment of the present disclosure, which is similar to the energy applicator 500 of FIG. 9, except for a tapered portion 920 extending distally from the distal end cap "P". Tapered portion 920 may terminate in a sharp tip 923 to allow for insertion into tissue with minimal resistance. In those cases where the energy applicator 600 is inserted into a pre-existing opening, the tip 923 may be rounded or flat. The shape and size of the tapered portion 920 may be varied from the configuration depicted in FIG. 11.

FIG. 12 shows an energy applicator 700, according to an embodiment of the present disclosure. As shown in FIG. 12, an outer jacket 1020 may be provided to the energy applicator 600 of FIG. 11. In some embodiments, the outer jacket 1020 is made of an insulating material, such as, for example, a polyimide or similar dielectric material. Outer jacket 1020 may be a water-cooled catheter formed of a material having low electrical conductivity. The outer surface of the outer jacket 1020 may be coated with a suitable lubricious substance, such as TEFLON®, to aid in the movement of the outer jacket 1020 in or through tissue as well as to aid in preventing tissue from sticking thereto.

Figure 13:
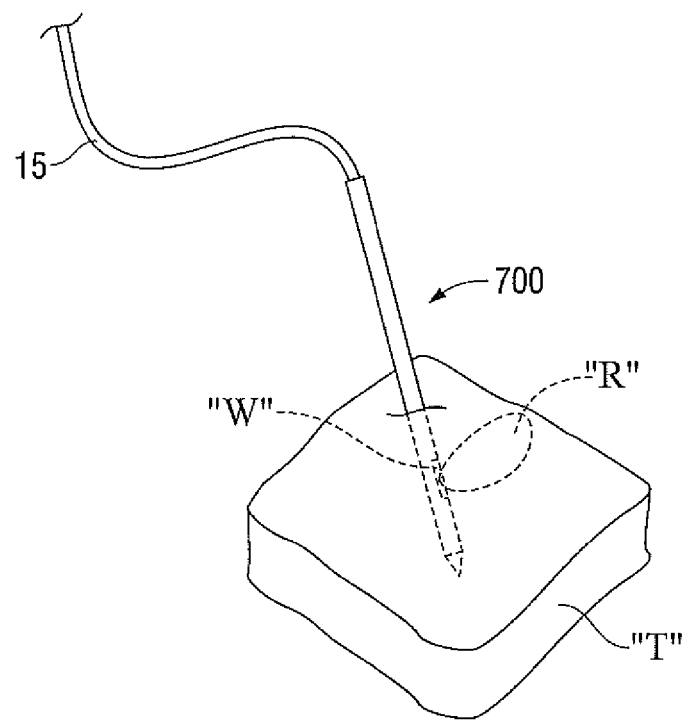
FIG. 13 is a diagrammatic representation of a radiation pattern of electromagnetic energy delivered into tissue by an energy applicator, such as the energy applicator of FIG. 12, according to an embodiment of the present disclosure.

FIG. 13 shows an embodiment of an energy applicator (e.g., 700 shown in FIG. 12) coupled to a transmission line 15 according to the present disclosure. Transmission line 15 may connect the energy applicator 700 to a power generating source, e.g., a microwave or RF electrosurgical generator. During a procedure, e.g., an ablation procedure, the energy applicator 700 is inserted into or placed adjacent to tissue "T" and energy is supplied thereto. Energy applicator 700 may be placed percutaneously or atop tissue. Ultrasound or computed tomography (CT) guidance may be used to accurately guide the energy applicator 700 into the area of tissue "T" to be treated.

Energy applicator 700 may be rotatable about a longitudinal axis "A-A" (shown in FIG. 2) such that the directional radiation pattern "R" rotates therewith. Examples of antenna assemblies rotatable about axis "A-A" such that any elongated radiation lobes rotates therewith are disclosed in commonly assigned U.S. patent application Ser. No. 12/197,405 filed on Aug. 25, 2008, entitled "MICROWAVE ANTENNA ASSEMBLY HAVING A DIELECTRIC BODY PORTION WITH RADIAL PARTITIONS OF DIELECTRIC MATERIAL".

Energy applicator 700 may include an indicia alignment mark (not shown) such as a colored strip or the like (e.g., to provide a visual cue to the surgeon to allow orientation of the direction of flow of the energy to coincide with the indicia alignment mark) and/or indicia graduation marks (not shown) for insertion depth reference (e.g., to indicate the position of the opening "W" relative to the surface of the tissue "T"). Examples of indicia alignment mark and the indicia graduation mark embodiments are disclosed in commonly assigned U.S. patent application Ser. No. 12/476,960 filed on Jun. 2, 2009, entitled "ELECTROSURGICAL DEVICES WITH DIRECTIONAL RADIATION PATTERN".

FIGS. 14 through 17 show various configurations of dielectric material at the site of a window (e.g., "W" shown in FIG. 13) of an energy applicator (e.g., 700 shown in FIG. 13) and examples of emitted radiation patterns, according to embodiments of the present disclosure.

FIG. 14 shows a cross-sectional view of an energy applicator 1400 and an emitted radiation pattern "R1" of microwave energy radiated therefrom. In FIG. 14, the window is approximately ½ the circumference of the elongated shaft 1493 thereof. A first dielectric member 1464 and a second dielectric member 1462 are coupled to an inner conductor 1420 at the site of the window. Inner conductor 1420 may be similar to the inner conductor 220 shown in FIG. 2. First and second dielectric members 1464, 1462 may have substantially the same diameter. Second dielectric member 1462 may be similar to the second dielectric segment 274 shown in FIG. 2. In the embodiment depicted in FIG. 14, the elongated shaft 1493 extends over the second dielectric member 1462. The window in the elongated shaft is filled with a radio frequency (RF) transparent material 1485, e.g., a glass fiber epoxy composite or polyimide.

FIG. 15 shows a cross-sectional view of an energy applicator 1500 and an emitted radiation pattern "R2" of microwave energy radiated therefrom. In the energy applicator 1500, the window is approximately ¼ the circumference of the elongated shaft 1593 thereof. A first dielectric member 1564 and a second dielectric member 1562 are coupled to the inner conductor 1420 at the site of the window. In the embodiment depicted in FIG. 15, the elongated shaft 1593 extends fully over the second dielectric member 1562 and partially over the first dielectric member 1564. The window in the elongated shaft 1593 of the energy applicator 1500 is filled with a RF transparent material 1585.

FIG. 16 shows a cross-sectional view of an energy applicator 1600 and an emitted radiation pattern "R3" of microwave energy radiated therefrom. In the energy applicator 1600, the window is approximately ⅘ the circumference of the elongated shaft 1693. A first dielectric member 1664 and a second dielectric member 1662 are coupled to the inner conductor 1420 at the site of the window. In the embodiment depicted in FIG. 16, the window and the RF transparent material 1685 disposed therein extends fully over the first dielectric member 1664 and partially over the second dielectric member 1664.

Figure 17:
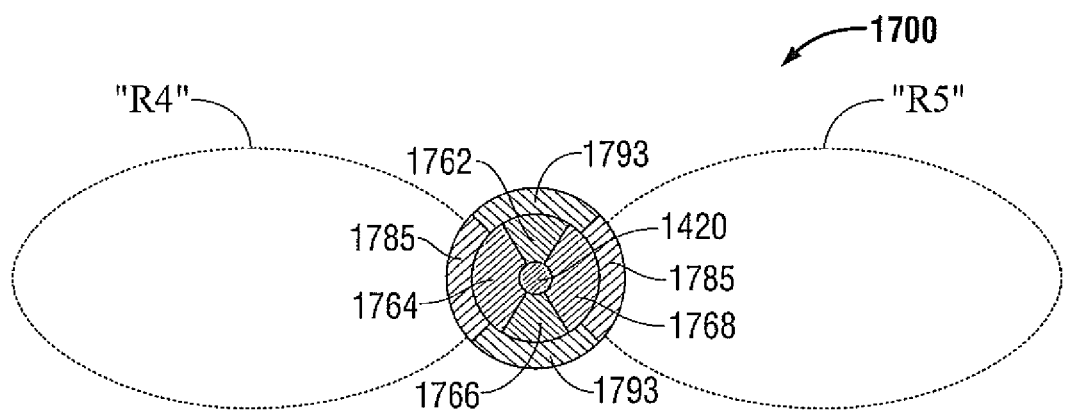
FIG. 17 is a cross-sectional view of still another embodiment of an energy applicator shown with a diagrammatic representation of an emitted radiation pattern according to the present disclosure.

FIG. 17 shows a cross-sectional view of an energy applicator 1700 having two windows and two emitted radiation patterns "R4" and "R5" of microwave energy radiated therefrom. In the energy applicator 1700, each of the two windows is approximately 114 the circumference of the elongated shaft 1793 thereof. In the embodiment depicted in FIG. 17, a RF transparent material 1785 is disposed in each of the windows. Energy applicator 1700 includes a first dielectric segment 1764, a second dielectric segment 1762, a third dielectric segment 1768 and a fourth dielectric segment 1766, each coupled to the inner conductor 1420. The shape and size of the first, second, third and fourth dielectric segments may be varied from the configuration depicted in FIG. 17.

Hereinafter, a method of manufacturing an energy applicator or probe having a dielectric loaded coaxial aperture with distally positioned resonant structure, in accordance with the present disclosure, is described with reference to FIG. 18. It is to be understood that the steps of the method provided herein may be performed in combination and in a different order than presented herein without departing from the scope of the disclosure.

Figure 18:
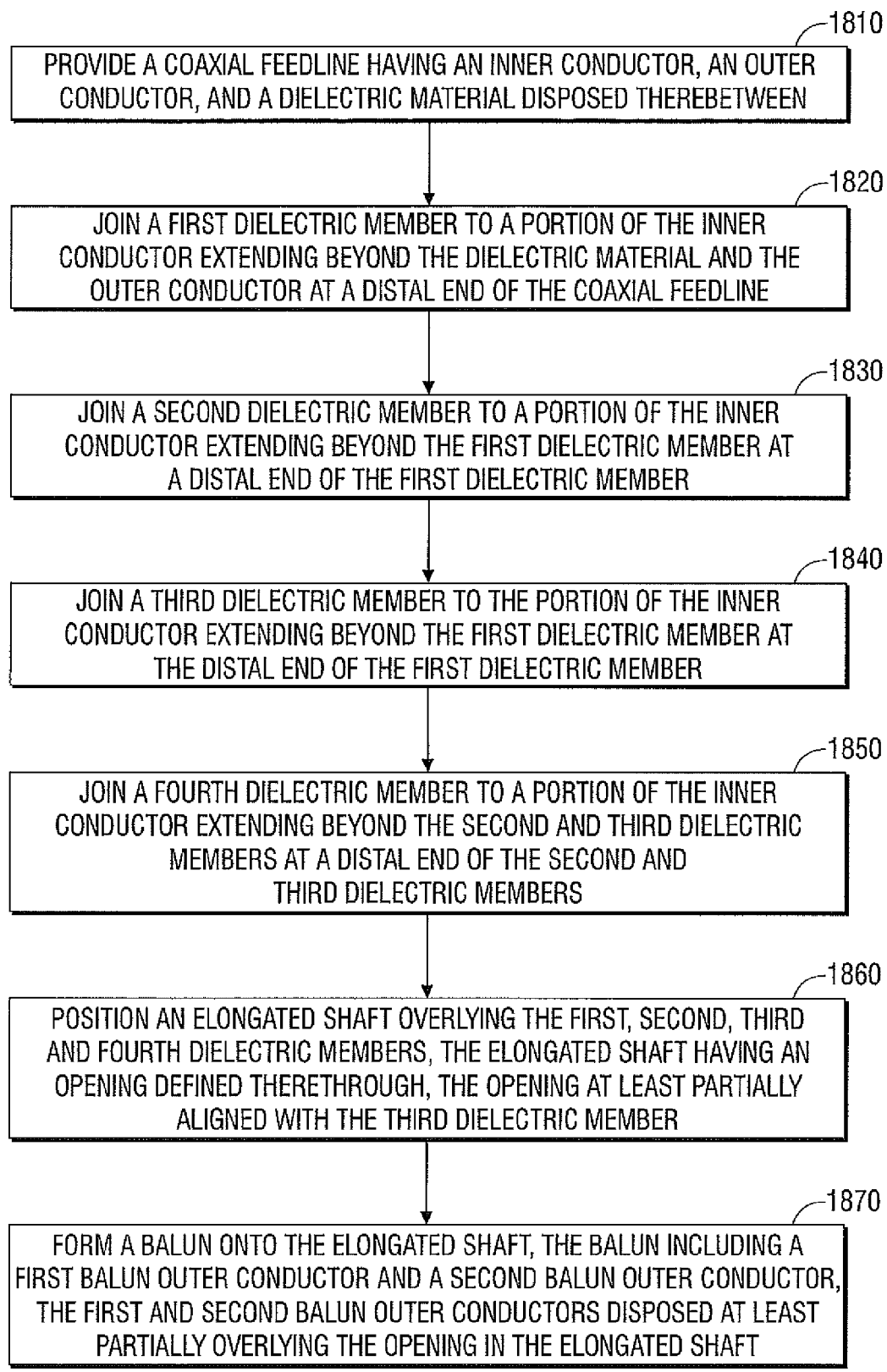
FIG. 18 is a flowchart illustrating a method of manufacturing an electrosurgical device according to an embodiment of the present disclosure

FIG. 18 is a flowchart illustrating a method of manufacturing an electrosurgical device according to an embodiment of the present disclosure. In step 1810, a coaxial feedline (e.g., 226 shown in FIG. 2) is provided. The coaxial feedline includes an inner conductor (e.g., 220 shown in FIG. 2), an outer conductor (e.g., 224 shown in FIG. 2), and a dielectric material (e.g., 222 shown in FIG. 2) disposed therebetween.

In step 1820, a first dielectric member (e.g., 244 shown in FIG. 3) is joined to a portion of the inner conductor (e.g., 22 shown in FIG. 2) extending beyond the dielectric material and the outer conductor at a distal end of the coaxial feedline. The first dielectric member may have a substantially cylindrical shape, and may be configured with a central channel (e.g., 245 shown in FIG. 2) extending longitudinally therethrough to accommodate the inner conductor.

In step 1830, a second dielectric member (e.g., 284 shown in FIG. 3) is joined to a portion of the inner conductor extending beyond the first dielectric member at a distal end of the first dielectric member. The second dielectric member may have a substantially half-cylindrical shape including a flat planar surface and a half cylindrical surface. The flat planar surface of the second dielectric member may be configured with a recess in the form of a groove (e.g., 287 shown in FIG. 2) extending longitudinally thereacross.

In step 1840, a third dielectric member shaft (e.g., 274 shown in FIG. 3) is joined to the portion of the inner conductor extending beyond the first dielectric member at a distal end of the first dielectric member. The third dielectric member may have a substantially half-cylindrical shape including a flat planar surface and a half cylindrical surface. The flat planar surface of the third dielectric member may be configured with a recess in the form of a groove defined therein (e.g., 277 shown in FIG. 2) extending longitudinally thereacross.

In step 1850, a fourth dielectric member shaft (e.g., 264 shown in FIG. 3) is joined to a portion of the inner conductor extending beyond the second and third dielectric members at a distal end of the second and third dielectric members. The fourth dielectric member may have a substantially cylindrical shape, and may be configured with a central channel defined therein (e.g., 265 shown in FIG. 2) extending longitudinally therethrough to accommodate the inner conductor.

In step 1860, an elongated shaft (e.g., 480 shown in FIG. 4) having an opening defined therethrough is positioned overlying the first, second, third and fourth dielectric members, such that the opening (e.g., 440 shown in FIG. 4) is aligned with the third dielectric member. In some embodiments, the third dielectric member is configured to fill the opening in the elongated shaft (e.g., 480). In some embodiments, the opening in the elongated shaft (e.g., 480) is filled with a RF transparent material (e.g., 1485, 1585, 1685, 1783 and 1787 shown in FIGS. 14 through 17).

In step 1870, a balun structure (e.g., 909 shown in FIG. 9), which includes a first balun outer conductor (e.g., 871 shown in FIG. 9) and a second balun outer conductor (e.g., 872 shown in FIG. 9) is formed onto the elongated shaft (e.g., 480 shown in FIG. 9), such that the first and second balun outer conductors (e.g., 871, 872) are each disposed at least partially overlying the opening in the elongated shaft (e.g., 480). Step 1870 may further include the steps of forming a balun insulator (e.g., 740 shown in FIG. 8) extending over an outer surface of the elongated shaft (e.g., 480 shown in FIG. 8), and positioning the first and second balun outer conductors (e.g., 871, 872) on the balun insulator (e.g., 740 shown in FIG. 9), wherein a distal end of the second balun outer conductor (e.g., 872) is positioned adjacent to a distal end of a balun short (e.g., "P" shown in FIG. 9).

The above-described electrosurgical devices for treating tissue and methods of directing electromagnetic radiation to a target volume of tissue may be used to provide directional microwave ablation, wherein the heating zone may be focused to one side of the electrosurgical device, thereby allowing clinicians to target small and/or hard to access tumors without having to penetrate the tumor directly or kill more healthy tissue than necessary. The presently disclosed electrosurgical devices may allow clinicians to avoid ablating or unnecessarily heating tissue structures, such as large vessels, healthy organs or vital membrane barriers, by placing the electrosurgical device between the tumor and tissue structure and directing the electromagnetic radiation toward the tumor and away from the tissue structure.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical device for directing energy to a target volume of tissue, comprising:
    a coaxial feedline having an inner conductor, an outer conductor coaxially disposed around the inner conductor, and a dielectric material disposed therebetween; and
    an antenna assembly, including:
        an extension of the inner conductor that extends distally beyond the outer conductor and the dielectric material at a distal end of the coaxial feedline into the antenna assembly;
        a first arcuate dielectric segment;
        a second arcuate dielectric segment, the first and second arcuate dielectric segments coupled one to the other along a longitudinal axis of the antenna assembly, surrounding a portion of the extension of the inner conductor that extends distally beyond the outer conductor and the dielectric material at the distal end of the coaxial feedline; and
        an elongated shaft overlying at least a portion of the second arcuate dielectric segment, the elongated shaft having an opening defined therethrough for passage of energy therethrough, the opening at least partially aligned with the first arcuate dielectric segment.

2. The electrosurgical device of claim 1, wherein the first arcuate dielectric segment defines a longitudinally-extending channel configured to receive at least a portion of the extension of the inner conductor that extends distally beyond the outer conductor and the dielectric material at the distal end of the coaxial feedline.

3. The electrosurgical device of claim 1, wherein the first and second arcuate dielectric segments each include at least one flat planar surface and an arcuate surface.

4. The electrosurgical device of claim 3, wherein, when the first and second arcuate dielectric segments are coupled one to the other, the at least one flat planar surface of the first arcuate dielectric segment is disposed in contact with the at least one flat planar surface of the second arcuate dielectric segment.

5. The electrosurgical device of claim 1, wherein the opening in the elongated shaft is filled with a RF transparent material.

6. The electrosurgical device of claim 1, wherein the first arcuate dielectric segment is configured to fill the opening in the elongated shaft.

7. The electrosurgical device of claim 1, wherein the elongated shaft is electrically coupled to the outer conductor of the coaxial feedline.

8. The electrosurgical device of claim 1, wherein a dielectric constant of the first arcuate dielectric segment is higher than a dielectric constant of the second arcuate dielectric segment.

9. An electrosurgical device for directing energy to a target volume of tissue, comprising:
    a coaxial feedline having an inner conductor, an outer conductor coaxially disposed around the inner conductor, and a dielectric material disposed therebetween; and
    an antenna assembly, including:
        an extension of the inner conductor that extends distally beyond the outer conductor and the dielectric material at a distal end of the coaxial feedline into the antenna assembly;
        a proximal cylindrical dielectric sleeve, disposed at the distal end of the coaxial feedline, surrounding a proximal portion of the extension of the inner conductor that extends distally beyond the outer conductor and the dielectric material at the distal end of the coaxial feedline;
        a distal cylindrical dielectric sleeve disposed distal to the proximal cylindrical dielectric sleeve;
        a first arcuate dielectric segment; a second arcuate dielectric segment, the first and second arcuate dielectric segments coupled one to the other along a longitudinal axis of the antenna assembly, wherein a dielectric constant of the first arcuate dielectric segment is higher than a dielectric constant of the second arcuate dielectric segment;
        wherein the first and second arcuate dielectric segments are disposed between the proximal cylindrical dielectric sleeve and the distal cylindrical dielectric sleeve;
        an elongated shaft overlying the proximal cylindrical dielectric sleeve, the first arcuate dielectric segment, the second arcuate dielectric segment and the distal cylindrical dielectric sleeve, the elongated shaft having an opening defined therethrough for passage of energy therethrough, the opening at least partially aligned with the first arcuate dielectric segment; and a balun structure disposed on the elongated shaft, the balun structure at least partially overlying the opening in the elongated shaft.

10. The electrosurgical device of claim 9, wherein at least one of the proximal cylindrical dielectric sleeve and the distal cylindrical dielectric sleeve includes a central channel extending longitudinally therethrough configured to accommodate a portion of the extension of the inner conductor.

11. The electrosurgical device of claim 9, wherein the balun structure includes a first balun outer conductor and a second balun outer conductor, each of the first and second balun outer conductors disposed at least partially overlying the opening in the elongated shaft.

12. The electrosurgical device of claim 9, wherein the opening in the elongated shaft is filled with a RF transparent material.

13. The electrosurgical device of claim 9, wherein the first arcuate dielectric segment is configured to fill the opening in the elongated shaft.

14. The electrosurgical device of claim 9, further comprising a tapered portion, disposed distal to the distal cylindrical dielectric sleeve, having a tip configured to penetrate tissue.

15. The electrosurgical device of claim 9, wherein the first and second dielectric segments each include at least one flat planar surface and an arcuate surface.

* * * * *